United States Patent [19]
Tamura et al.

[11] Patent Number: 6,156,519
[45] Date of Patent: Dec. 5, 2000

[54] (→)-β- D-GLUCAN BINDING PROTEIN, AN ANTIBODY RECOGNIZING THE PROTEIN AND USE THEREOF

[75] Inventors: Hiroshi Tamura; Shigenori Tanaka, both of Tokyo, Japan

[73] Assignee: Seikagaku Corporation, Tokyo, Japan

[21] Appl. No.: 08/793,679

[22] PCT Filed: Aug. 31, 1995

[86] PCT No.: PCT/JP95/01735

§ 371 Date: Jun. 2, 1997

§ 102(e) Date: Jun. 2, 1997

[87] PCT Pub. No.: WO96/06858

PCT Pub. Date: Mar. 7, 1996

[30] Foreign Application Priority Data

Sep. 1, 1994 [JP] Japan .................................. 6-232024

[51] Int. Cl.$^7$ ......................... G01N 33/53; G01N 33/579; C07K 14/435; C07K 16/18
[52] U.S. Cl. ........................ 435/7.1; 435/7.31; 435/7.32; 435/7.8; 435/7.93; 435/7.94; 435/7.95; 435/23; 435/962; 530/350; 530/388.2; 530/389.1; 530/391.1; 530/396; 530/413; 530/857
[58] Field of Search ....................... 435/7.1, 7.31, 435/7.32, 7.93, 7.94, 7.95, 13, 23, 184, 962, 7.8; 436/518, 63, 69; 530/350, 388.2, 388.25, 388.26, 389.1, 389.3, 391.1, 396, 413, 806, 857

[56] References Cited

U.S. PATENT DOCUMENTS

| | | | |
|---|---|---|---|
| 4,414,336 | 11/1983 | Watanabe et al. | 435/18 |
| 5,266,461 | 11/1993 | Tanaka | 435/7.21 |
| 5,582,172 | 12/1996 | Papisov et al. | 128/653.4 |
| 5,585,248 | 12/1996 | Ashida et al. | 435/25 |

OTHER PUBLICATIONS

Quigley et al., 1991. Reaction of proteinases with α2–macroglobulin from the American horseshoe crab, *Limulus*. Journal of Biological Chemistry 266(29): 19426–19431.

Quigley et al., 1985. A homologue of α2–macroglobulin purified from the hemolymph of the horseshoe crab, *Limulus polyphemus*. Journal of Biological Chemistry 260(23): 12715–12719.

Iwaki et al., 1996. Molecular cloning of *Limulus* α2–macroglobulin. Eur. J. Biochem. 242:822–831.

Armstrong et al., 1994. α2–M in the horseshoe crab. A structural and functional invertebrate homologue. Annals of the New York Academy of Sciences 737: 188–201.

Tamura et al., 1996. Purification and characterization of a (1–3)–β–D–glucan–binding proteinb form horseshoe crab (*Tachypleus tridentatus*) amoebocytes. Carbohydrate Research 295: 103–116.

Enghild et al., 1996 α–Macroglobulin from *Limulus polyphemus* exhibitsproteinase inhibitory activity and participates in a hemplytic system. Biochemistry 29: 10070–10080.

*Primary Examiner*—James C. Jousel
*Assistant Examiner*—James L. Grun
*Attorney, Agent, or Firm*—Testa, Hurwitz & Thibeault, LLP

[57] ABSTRACT

A (1→3)-β-D-glucan binding protein obtainable by affinity chromatography or gel filtration of an extract of horseshoe crab amoebocytes and having a molecular weight of about 580 kDa, as determined by gel filtration under non-reducing conditions, and about 170 kDa, as determined by SDS-PAGE under reducing conditions, is provided.

An antibody which selectively recognizes the protein is also provided. Methods for detecting or removing (1→3)-β-D-glucan in or from a sample using the protein and antibody are disclosed.

8 Claims, 8 Drawing Sheets

(→)-β- D-GLUCAN BINDING PROTEIN, AN ANTIBODY RECOGNIZING THE PROTEIN AND USE THEREOF

FIELD OF THE INVENTION

This invention relates to a (1→3)-β-D-glucan binding protein or variants thereof obtained from horseshoe crab amoebocytes and an antibody thereto.

Further, the present invention relates to a (1→3)-β-D-glucan assay agent composed of said protein, a kit composed of said protein and said assay agent, a kit composed of said protein and said antibody, and the method for assaying (1→3)-β-D-glucan using said protein.

In addition, this invention relates to a (1→3)-β-D-glucan removing agent composed of the protein and a carrier bound to the protein and a method for removing (1→3)-β-D-glucan using the removing agent.

Furthermore, this invention relates to a method for inhibiting activation of factor G which may exist in horseshoe crab amoebocyte lysate using the protein.

Still further, this invention relates to a method for assaying endotoxin using the protein.

BACKGROUND OF THE INVENTION

In 1964, coagulation or gel formation of horseshoe crab, amoebocyte lysate (hereinafter may be abbreviated LAL), with a very small amount of an intracellular toxin of Gram negative bacteria (hereinafter abbreviated as endotoxin (Et) or lipopolysaccharide (LPS)) was discovered, and multiple factors, serine protease precursors, including Et (LPS) sensitive factor (factor C), participating in the gel formation have been found. This reaction is composed of a cascade mechanism which resembles to the coagulation system of blood of mammals, and similar mechanisms have also been reported in the other invertebrates LAL has been known to react with a very small amount of (1→3)-β-D-glucan (hereinafter abbreviated as β-glucan) to cause gel formation in addition to Et, and a sensitive factor G which recognizes β-glucan has been found. An induction of gel formation as well as Et by a quite different coagulation cascade route (factor G system) from a route by way of factor C (factor C system) has been elucidated. Further, β-glucan is a constructive polysaccharide of fungal cell wall and this route is presumed to be closely related to a defense system of a living body as well as factor C system, Heretofore, β-glucan binding protein such as blood coagulating factor G of horseshoe crab (FEBS Lett., 129, 318–321 (1981)), β-glucan recognizing protein of silkworm (prophenol oxidase) (J. Biol. Chem., 263, 12056–12062 (1988)), β-glucan receptor of human monocytes (J. Exp. Med., 173, 1511–1520 (1991)), an adjuvant receptor accompanied with localized opsonin formation (J. Immunol., 124, 3307–3315 (1985)), β-glucan elicitor to plant cells (J. Cell Biol., 78, 627 (1978)), a glucan binding protein derived from *Streptococcus sobrinus* (Infect Immun., 60 (12) 5291–5293 (1992)) and β-glucan specific lectin derived from great wax moth (*Galleria mellonella L.*, (Matha V., 64, 35–42 (1990)) have been reported.

DISCLOSURE OF THE PRESENT INVENTION

The inventors of the present invention have been investigating the gel formation factor in LAL and found a protein which specifically binds to β-glucan to inhibit the activation of factor G, and isolated the protein. Furthermore, the inventors of the present invention found an antibody which selectively recognizes the protein.

Therefore, the inventors of the present invention investigated the characteristic features of these proteins and the antibody and found their uses.

The object of the present invention is to provide a novel protein which specifically binds to such β-glucan and its antibody and to apply them for the assay of β-glucan and endotoxin, removal of β-glucan, and further for the treatment of fungal infections.

The present invention relates to a β-glucan binding protein obtained from horseshoe crab amoebocytes, purified with sodium dodecylsulfate-polyacrylamide gel electrophoresis (SDS-PAGE) to give a single band, and having the following physicochemical properties.

(1) Molecular weight: About 580 k dalton (gel filtration method under non-reducing conditions) and about 170 k dalton (SDS-PAGE under reducing conditions).
(2) Isoelectric point: About 9.2
(3) UV absorption spectrum: maximum at 280 nm.
(4) Solubility: Easily soluble in water
(5) Color: White.

The N-terminal amino acid sequence is as shown below.
Lys-Ser-Gly-Phe-Ile-Leu-Thr-Ala-Pro-Lys-Ser-Leu-Thr-Leu-Gly-Arg-Asn-Asn-Arg-Leu-Asn-Leu-His-Leu-Phe-Asp-Ile-Asn-—Thr-Asn-Gly-Phe-Xaa-Arg-Ile-Gly-Val-Lys-Asp-Gln-Asn-Asp-Phe-Asn-(SEQ ID NO:1)

(wherein, Xaa represents one of naturally occurring amino acids).

The present invention also includes variants of said protein.

The variants in the present invention are functionally equal to the aforementioned protein and those being substituted, deleted or added with an amino acid without substantial influence on the functions.

Further preferably, the variants in the present invention have high homogeneity in the amino acid sequence and have substantially equal effect to the aforementioned protein (hereinafter referred as protein including these variants).

The present invention further relates to the following antibody, glucan assay agent and assay kit using the antibody, and a method for assaying glucan.
(1) An antibody which selectively recognizes aforementioned protein.
(2) A (1→3)-β-D-glucan assay agent composed of optionally labelled aforementioned protein.
(3) A (1→3)-β-D-glucan assay kit composed of aforementioned protein and assay optionally labeled aforementioned antibody.
(4) A 1→3)-β-D-glucan assay kit composed of aforementioned protein and said assay agent.
(5) A method for assaying (1→3)-β-D-glucan which comprises reacting aforementioned protein with (1→3)-β-D-glucan in a sample followed by detection of said complex.
(6) The assay method shown in above (5) wherein the detection of aforementioned complex is carried out using the aforementioned antibody, or an antibody labelled or capable of being labelled.
(7) A method for assaying (1→3)-β-D-glucan which comprises forming a sandwich form complex wherein (1→3)-β-D-glucan in a sample is held between the protein or variants thereof immobilized or capable of being immobilized on a solid phase and the protein or variants thereoflabelled with a labelling substance immobilizing said complex on the solid phase, in case when the protein or variants thereof are capable of being immobilized on the solid phase, separating the solid phase from a liquid phase and detecting the labelled substance in either one of the both phases.

Further, the present invention relates to a glucan-removing agent and a method for removal from a sample containing such glucan (8) A (1→3)-β-D-glucan-removing agent composed of aforementioned protein or a carrier having immobilized above mentioned protein.

(9) A method for removing (1→3)-β-D-glucan which comprises reacting aforementioned protein optionally immobilized on a carrier with (1→3)-β-D-glucan in a sample to form a complex and removing said complex from the sample.

Further, the present invention relates to a method for inhibiting activation of factor G.

(10) A method for inhibiting activation of factor G which comprises mixing the protein or variants thereof with horseshoe crab amoebocytes lysate, or mixing a sample with said protein or variants thereof, followed by mixing said sample with the horseshoe crab amoebocyte lysate to inhibit activation of factor G which may exist in said horseshoe crab amoebocyte lysate.

Further, the present invention relates to a method for assaying an endotoxin.

(11) A method for assaying endotoxin contained in a sample containing (1→3)-β-D-glucan by Limulus reaction using horseshoe crab amoebocyte lysate which comprises mixing the sample with the protein or variants thereof, or mixing said lysate with said protein or variants thereof prior to Limulus reaction. These β-glucan binding proteins (herein after may be referred as GBP) of the present invention can be extracted from amoebocytes of horseshoe crab such as *Tachypleus tridentatus, Tachypleus gigas, Limulus polyphemus* and *Carcinoscorpius rotundicauda* by application of conventional low tension extraction method (for example, J. Biochem., 80, 1101–1021 (1976)).

Practically, horseshoe crab amoebocytes were mixed with 0.02M Tris-HCl buffer, pH 8.0 cooled to 0–4° C., stirred at 0–4° C. and extracted. The extract was centrifuged under cooling to give a supernatant, lysate. The resultant supernatant, lysate, contains various coagulation factors including proclotting enzyme, coagulogen, factors G, factor B, factor C, GBP, and anti-LPS factor. The lysate is charged to a dextran sulfate-Sepharose CL-6B affinity column (dextran sulfate, Sepharose CL-6B (Pharmacia)) equilibrated with 0.02–0.05M Tris-HCl buffer, pH 7.0–8.5, containing 0–0.2M NaCl by a known method (Anal. Biochem., 60, 149–152 (1974)) and eluted with said buffer containing 0.2–0.5M NaCl. The fractions showing GBP activity are collected from eluate to give a fraction containing factor B, factor C and GBP. The fractions are lyophilized and purified with gel filtration chromatography.

The gel filtration chromatography is carried out with Sephacryl S-300 HR (High Resolution) column (Pharmacia) equilibrated with 0.02–0.0M Tris-HCl buffer, pH 6–5–8.5, containing 0.4–1M NaCl, or Cellulofine GCL-2000 m column (Seikagaku Corporation). The elution is carried out with a buffer used for equilibration and a similar chromatographic procedure is preferably repeated at least twice.

The eluate of gel filtration chromatography is fractionated and GBP activity of each fraction is determined to collect the active fractions. Factors B and C, and GBP are almost completely separated by the first chromatography and purified GBP is obtained by re-chromatography using similar column conditions. The resulting fractions are collected and lyophilized to give GBP of the present invention. The purified GBP is white powder and easily soluble in water. shows a single band in polyacrylamide gel electrophoresis (PAGE) and exhibits aforementioned physicochemical properties.

The GBP of the present invention has a N-terminal amino acid sequence found by the inventors and can be prepared by known methods of gene technology, for example, preparation of DNA primer from said sequence, preparation of DNA encoding GBP from cDNA library obtained from horseshoe crab amoebocytes and integration of the DNA in a vector to give a recombinant, followed by expression with known methods.

GBP activity in the present invention can be determined by adding 0.05 ml of 50 pg/ml 0.01M NaOH aqueous solution of Pachyman prepared from *Porisa cocos* by the method of Saito et al. (Agri. Biol, Chem., 32, 1261–1269 (1968)) to each 0.05 ml fraction of above mentioned chromatography, incubating at 37° C. for 10 min., adding 0.04 ml of factor G prepared from amoebocyte lysate of *Tachypleus tridentatus* by the method of Obayashi At al (Clin. Chim. Acta, 149, 55–65 (1985)), 0.02 ml of proclotting enzyme, 0.01 ml each of 1M $MgSO_4$ and 2M Tris-HCl buffer, pH 8.0, and 0.02 ml of 5 mM t-butoxycarbonyl-L-leucyl-glycyl-L-arginine-p-nitroanilide (Boc-Leu-Gly-Arg-pNA) as a substrate of clotting enzyme to the resulting mixture, and reacting at 37° C. for 20 min The liberated p-nitroaniline is developed by diazo coupling and determined by absorbance at 545 nm. The inhibitory activity is determined from relative activity obtained by using water instead of the sample to make factor G activity as 100% (control). The inhibition of activation of factor G is due to the binding of GBP and β-glucan (see Examples shown later). Thus, the inhibitory activity of factor C is made as GSP activity.

Further, the purity of GBP of the present invention may be assayed by polyacrylamide gel electrophoresis (PAGE) at pH 7.0–8.0 and 5–7.5% gel or at pH 4–5 and 5–7.5% gel, or SDS PAGE (at pH 7.0–8.0, 6–7.5% gel and 0.1–0.2% SDS) or isoelectric point electrophoresis (IEF).

The molecular weight of GBP can be determined by SDS-PAGE, gel filtration with Sephacryl S-300 HR or Cellulofine GCL-2000 m, precipitation equilibrium by interference optical system, sedimentation assay with ultracentrifugation, viscosity, light scattering, osmotic pressure determination with collodion film, analysis of amino acid or laser ion mass spectrometry.

However, the GBP of the present invention is a substance with affinity to β-glucan having a specific structure, and has larger molecular weight than those of conventional proteins, thus it is difficult to obtain exact value in physical analysis such as gel filtration using insoluble carrier having glucoside biding or mass spectrometry Therefore, selection of carriers and conditions without these interference are required.

The UV absorption spectrum of GBP of the present invention is shown in FIG. 7 indicating maximum absorption at 280 nm.

The N-terminal amino acid sequence of GBP of the present invention is shown in the sequence table sequence No. 1.

Further, the present invention includes aforementioned variants

The GBP of the present invention specifically binds to β-glucan having (1→3)-β-D-polyglucoside structure and neutralizes biochemical and immuno-pharmacological properties of β-glucan including activation ability of horseshoe crab factor G. Further the GBP of the present invention neutralizes branched chain (1→3)-β-D-glucan having intramolecular side chain such as (1→6)-β-D- or (1→4)-β-D- as well as straight chain (1→3)-β-D-glucan.

(Antibody)

An antibody which selectively recognizes GBP of the present invention (hereinafter may be referred as anti-GBP antibody) can be obtained using purified GBP as an antigen and includes anti-serum, polyclonal antibody and monoclonal antibody against the antigen.

The preparation of polyclonal antibody used in the present invention can be prepared by administrating said antigen to animals to be immunized such as rabbits and goats and further purifying the resultant anti-serum Administration of said antigen to animals to be immunized together with an adjuvant is preferable for stimulation of antibody producing cells.

The preparation of monoclonal antibody used in the present invention can be carried out by intraperitoneal administration of said antigen to mice or rats, extraction of spleen, cell fusion of cells obtained from the spleen and myeloma cells being tumor cell strain to establish a hybridoma. The produced hybridoma is continuously in vitro proliferated and screened to give a cell strain which continuously produce a specific antibody against aforementioned antigen. The selected cell strain is in vitro cultured or in vivo cultured in abdominal cavity of mouse to give a large amount of monoclonal antibody lymphnode cells and Lymphocytes in peripheral blood other than spleen cells can be used for the cell fusion. Myeloma cells are preferably derived from homologous cell strain in comparison with those of xenogenic cells to give stable antibody-producing hybridoma.

The purification of the resultant polyclonal and monoclonal antibodies is carried out by salting out with neutral salts such as sodium sulfate and ammonium sulfate, precipitation with cooled alcohol, selective precipitation with polyethylene glycol or isoelectric point, electrophoresis, deabsorption method with ion exchanger such as DEAE-carrier and CM-carrier, protein A and hydroxyapatite adsorbent, gel filtration and ultracentrifugation method.
(Assay method)

The GBP of the present invention specifically binds to β-glucan having (1→3)-β-D-polyglucoside structure [hereinafter may be regarded as (1→3)-β-D-glucan] and can be used for the assay of (1→3)-β-D-glucan by reacting said GBP with (1→3)-β-D-glucan in a samples to form a complex and detecting said complex.

The assay of (1→3)-β-D-glucan of the present invention may be illustrated, for example:

A sandwich form complex composed of (1→3)-β-D-glucan in a sample held between GBP immobilized or capable of being immobilized on a solid phase and a labelled GBP is formed When the protein or its variants is/are capable of being immobilized on a solid phase, then said complex is immobilized on a solid phase to separate the solid phase from liquid phase. Then, a labelled substance in either phase is determined according to the properties of said labelled substance to assay (1→3)-β-D-glucan.

The assay of (1→3)-β-D-glucan can be carried out, for example, by adding of a sample containing (1→3)-β-D-glucan to GBP immobilized on a solid phase to bind said GBP to (1→3)-β-D-glucan and simultaneously or successively adding GBP labelled with a labelling agent beforehand to form sandwich form complex composed of said (1→3)-β-D-glucan held between said GBP and labelled GBP, or by mixing said labelled GBP with a sample containing (1→3)-β-D-glucan to give a bound substance of said labelled GBP and (1→3)-β-D-glucan, adding the bound substance to GBP immobilised on a solid phase to form said sandwich form complex. The solid phase immobilized with said complex and liquid phase are separated and the labelled substance in either phase, for example, labelled substance of said complex immobilized on a solid phase, is detected and assaied by a method suitable for said labelled substance.

The labelled GBP used in the present invention can be prepared by direct labeling with a labeling substance such as enzymes (peroxidase, alkallnephosphatase, β-galactosidase, etc.), radioactive isotopes ($^{125}$I, $^{131}$I and $^{3}$H), fluorescent substance (fluorescein isothiocyanate and umbelliferone, etc,), chemiluminescent substance (luminol, etc,), or other substances (biotin, avidin, preferably streptoavidin, etc.) by a known method.

The labeling of GBP is carried out by selecting a known method suitable for the labeling substance, for example, glutaraldehyde method, periodic acid cross-linking method, maleimide crosslinking method and carbodiimide method for the labeling of enzymes, chloramine T method and lactoperoxidase method for the labeling of radioactive isotopes (see Continued Biochemistry Experimental Studies, 5 immuno-biochemical studies, Tokyo Kagaku Dozin, 1986, European Patent Specification No, 0163041).

The GBP of the present invention is immobilized on a solid phase such as a solid insoluble carrier, e.g. microplate, beads, tubes, membranes, latices, test tubes, sheets of filter paper, agarose, polyacrylamides, cellulose and dextran by application of conventional physical adsorption, covalent bond or inclusion methods known as methods for preparation of immobilized enzyme (Immobilized Enzymes, 1975, Kodansha Pub. Co., Ltd., p. 9–75). Particularly, physical adsorption method is simple and preferable. The site without binding to GBP is preferably blocked with serum albumin, gelatin, and milk protein.

The assay of the present invention is explained in detail. GBP is immobilized on a solid phase by various methods. For example, GBP is dissolved in a phosphate or carbonate buffer at pH 9–10, added to a solid phase and kept at 4° C. for 6–14 hrs to immobilize GBP. After immobilization, a block mass is added beforehand to cover sites wherein GBP is not immobilized, The blocking mass includes serum albumin, serum or milk protein isolated from cattle.

Then, a sample containing (1→3)-β-D-glucan is added to the aforementioned solid phase having immobilized GBP to bind (1→3)-β-D-glucan to said GBP. Samples containing (1→3)-β-D-glucan, such as blood or body fluid of human being, cattle, rats and mice, and other samples shown later will be used as it is. After binding (1→3)-β-D-glucan, the solid phase is preferably washed with a phosphate buffer containing Tween surfactants and the like.

A labelled GEP is added to the resultant solid phase bound to (1→3)-β-D-glucan to give the labelled products. This procedure provides a sandwich form complex holding (1→3)-β-D-glucan between said GBP and said labelled GBP.

Then, the labeled substance in said sandwich form complex is quantitatively assaied to find the amount of (1→3)-β-D-glucan. Assay methods of labelled substances vary with the characteristic features of labeled substance. For example, when biotin is used as a labeling substance, an enzyme bound to avidin or streptoavidin is added to a solid phase or an insoluble carrier having sandwich form complex to bind the enzyme to the complex by way of avidin. The changes of substrate due to enzymic reaction of said enzyme can be assaied.

A calibration curve exhibiting the relationship between concentrations of (1→3)-β-D-glucan and labelled substance is prepared for quantitative assay of (1→3)-β-D-glucan in unknown sample using the assay results for unknown sample and said calibration curve.

Determinations method of the present invention include addition of labeled GBP to immobilized (1→3)-β-D-glucan (for example, (1→3)-β-D-glucan in cells or tissues, or (1→3)-β-D-glucan physically or chemically bound on insoluble carriers), to form a complex of said (1→3)-β-D-glucan and said GBP followed by detection or quantitative assay of (1→3)-β-D-glucan with the labelled substance in the complex.

Additionally, the assay method of the present invention may be carried out by adding GBP labelled with a labeling substance to the immobilized (1→3)-β-D-glucan (for example, (1→3)-β-D-glucan existing in cells or tissue and (1→3)-β-D-glucan physically or chemically bound to insoluble carrier) to form a complex of said GBP and (1→3)-β-D-glucan and detecting or assaing (1→3)-β-D-glucan with labelled substance in the complex.

Additionally, the assay method of the present invention may be carried out by additing GBP to the immobilized (1→3)-β-D-glucan to form a complex of said GBP and (1→3)-β-D-glucan, addition of an antibody which selectively recognizes GBP, labeling said antibody with a substance which specifically recognizes said antibody and detecting or assaying (1→3)-P-D-glucan with said substance. Formation of said complex, adding said antibody labelled with a labeling substance in advance, followed by detection and assay of (1→3)-β-D-glucan with said labelled substance may also be illustrated.

Substances which specifically recognizes said antibody include, for example, a compound obtained by labeling anti-immunoglobulin antibody with labeling substances (for example, biotin, avidin, enzyme, isotope, fluorescent pigment, chemiluminescent substances) by known method.

The assay kit of the present invention is composed of GBP and labelled GBP. The GBP requires to be immobilized on a solid phase prior to the assay using the kit. However, the process may be left out by immobilizing said GBP on a solid phase in advance.

The kit of the present invention is composed of GBP and an antibody which selectively recognizes GBP, however, may further be added with labelled anti-immunoglobulin antibody.

The kit of the present invention is composed of GBP and labelled anti-GBP antibody.

The kit of the present invention may further be added with aforementioned solid phase, a reagent which recognizes the labelled substance, a buffer, and a standard substance.
(Removal)

(1→3)-β-D-glucan in a sample can be removed by reacting GBP of the present invention with (1→3)-β-D-glucan to form a complex and isolating and removing said complex. The isolation and removal of said complex may be carried out by application of known isolation method of proteins. Preferably, a method for contacting a carrier having immobilized GBP, more preferably on insoluble carrier with (1→3)-β-D-glucan in the sample to form a complex of said GBP and (1→3)-β-D-glucan and isolating and removing the complex is carried out.

The carriers used may take various forms such as films (filters, hollow fibers, tubes and flat films), particles, latices, chips, powder, and microplates. (1→3)-β-D-glucan free carrier is preferably used.

Binding of the carrier to GBP is performed by physical binding of GSP to carriers such as polystyrene and polypropylene and the like or chemical binding of GBP to carriers such as polyamides, cellulose, agarose, polyacrylamides, dextrans, vinyl polymers (porous copolymers of glycidyl methacrylate and ethylene glycol dimethacrylate) The chemical binding includes diazo method of diazo coupling reaction using aromatic amino group in the carrier, CNBr method of peptide binding by activated hydroxyl group in the carrier with CNBr, acid azide method of peptide binding using hydrazine derivatives of the carrier, alkylation methods of alkylation of protein using reactive functional group such as halogen in the carrier, cross-linking method of the carrier and free amino group in protein using a cross-linking agent such as glutaraldehyde which reacts with free amino group, carbodiimide method, epoxy activating method, and further selection of a suitable method from known binding methods by way of a spacer for the binding of GBP.

The contact of carrier bound to GBP and a sample containing (1→3)-β-D-glucan is performed by known solid-liquid contact method For example, passing a sample through a filter formed carrier; passing a sample through a column filled with particle carrier; placing a sample in a well of microplate formed carrier, allowing to stand for a predetermined period, followed by isolation of the sample; and addition of a sample in voluntary form of carrier, shaking for a predetermined period or standing followed by conventional solid-liquid separation-isolation method (filtration, centrifugation, suction and decantation) may be illustrated for removing (1→3)-β-D-glucan from samples.

In Et assay by limulus reaction using horseshoe crab amoebocyte lysate, said GBP is added to LAL or a sample to form a complex with β-glucan and to inhibit the activation of β-glucan sensitive factor (factor C). Thus, specific assay of Et in the sample containing β-glucan may be carried out due to factor C system reaction in LAL without influence of β-glucan.

As explained above, the GSP of the present invention may be used for the detection and assay reagent of β-glucan and Et. Further, β-glucan is a constructive polysaccharide of fungal cell wall and GBP may affect the proliferation of fungi by binding to said polysaccharide. Thus, the GBP of the present invention is expected to be developed as medicines, particularly anti-fungal agent.

The assay and removal methods of (1→3)-β-D-glucan of the present invention can be applied for the detection and removal of (1→3)-β-D-glucan contained in body fluids such as serum, plasma, urine and cerebrovascular fluid, parenteral medicines, infusion solutions, water for injection and biological pharmaceutical preparations.

The endotoxin assay of the present invention can be applied to similar samples shown above for the detection of endotoxin contained in the samples.

THE BEST MODE TO CARRY OUT THE PRESENT INVENTION

The best bode for carrying out the present invention is shown by Examples.

In the present Examples, all glass tools used in the experiments were heat sterilized at 250° C. for two hours to make β-glucan free Some reagents were treated with active charcoal and autoclaved at 121° C. for 20–90 min. to make β-glucan free. The following procedures were carried out under β-glucan free conditions.

EXAMPLE 1

Purification and Physicochemical Properties of GBP (1) Purification of GBP

Under 40° C., 2.5 L of hemolymph of Japanese horseshoe crab (Tachypleus tridentatus) were centrifuged at 1,500 rpm for 10 min. In about 50 g of precipitated fraction of blood cells, amoebocytes, 500 ml of 0.02M Tris-HCl buffer (pH 8.0) was added and homogenized with a homogenizer (Polytron$^{RT}$ 10, Kinematica Corp.) and extracted. The resultant mixture was centrifuged at 10,000×G for 30 min. at 40° C. to give 450 ml of a supernatant, lysate.

Figure 1:
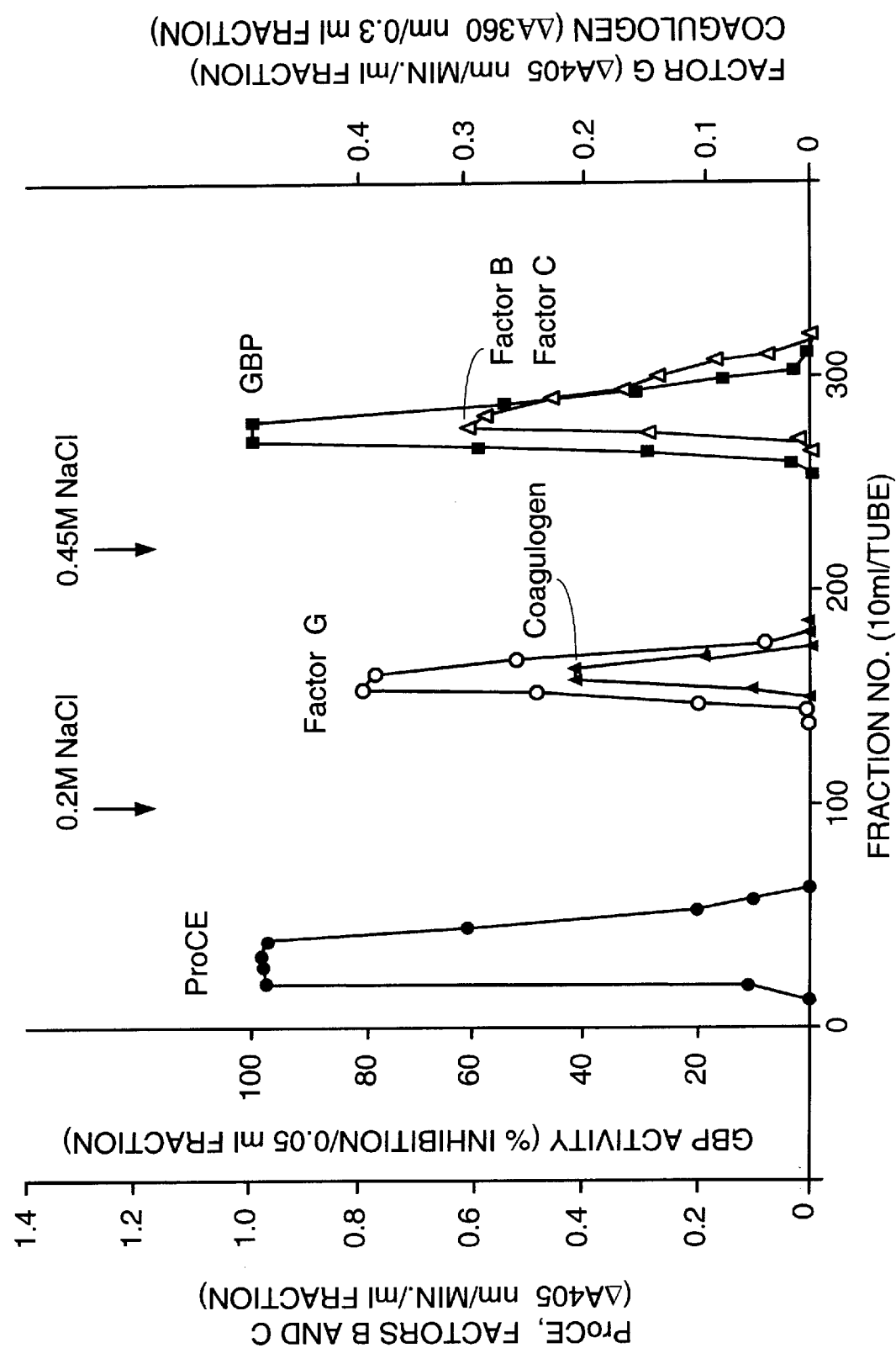
FIG. 1 shows an elution pattern of horseshoe crab amoebocytes, byoate using sulfate-Sepharose CL-6B column chromatography by Example 1.

The whole lysate was applied to a dextran sulfate-Sepharose CL-6B column (5×23 cm) equilibrated with 0.02M Tris-HCl buffer (pH 8.0), washed with 1.0 L of the same buffer, eluted with 1.5 L of 0.02M Tris-HCl buffer (pH 8.0) containing 0.2M NaCl, then with 1.5 L of 0.02M Tris-HCl buffer (pH 8.0) containing 0.45M NaCl to give each 10 ml fractions. The activity of eluted fractions were determined by the method of Obayashi et al. (Clin. Chim. Acta, 149, 55–65 (1985)). Activity of Proclotting enzyme, and factors B, C and G were determined with absorbance at 405 nm and activity of coagulogen was determined with absorbance at 360 nm. The GBP activity was determined by the method described later (see Example 2-(4), Experiment 3, water was used as a control instead of GBP). The results are shown in FIG. 1. GBP was found in fractions eluted with 0.45M NaCl and strongly inhibited the activation of factor G with β-glucan. The 310 ml of this fraction were collected in a egg plant flask and lyophilized.

Figure 2:
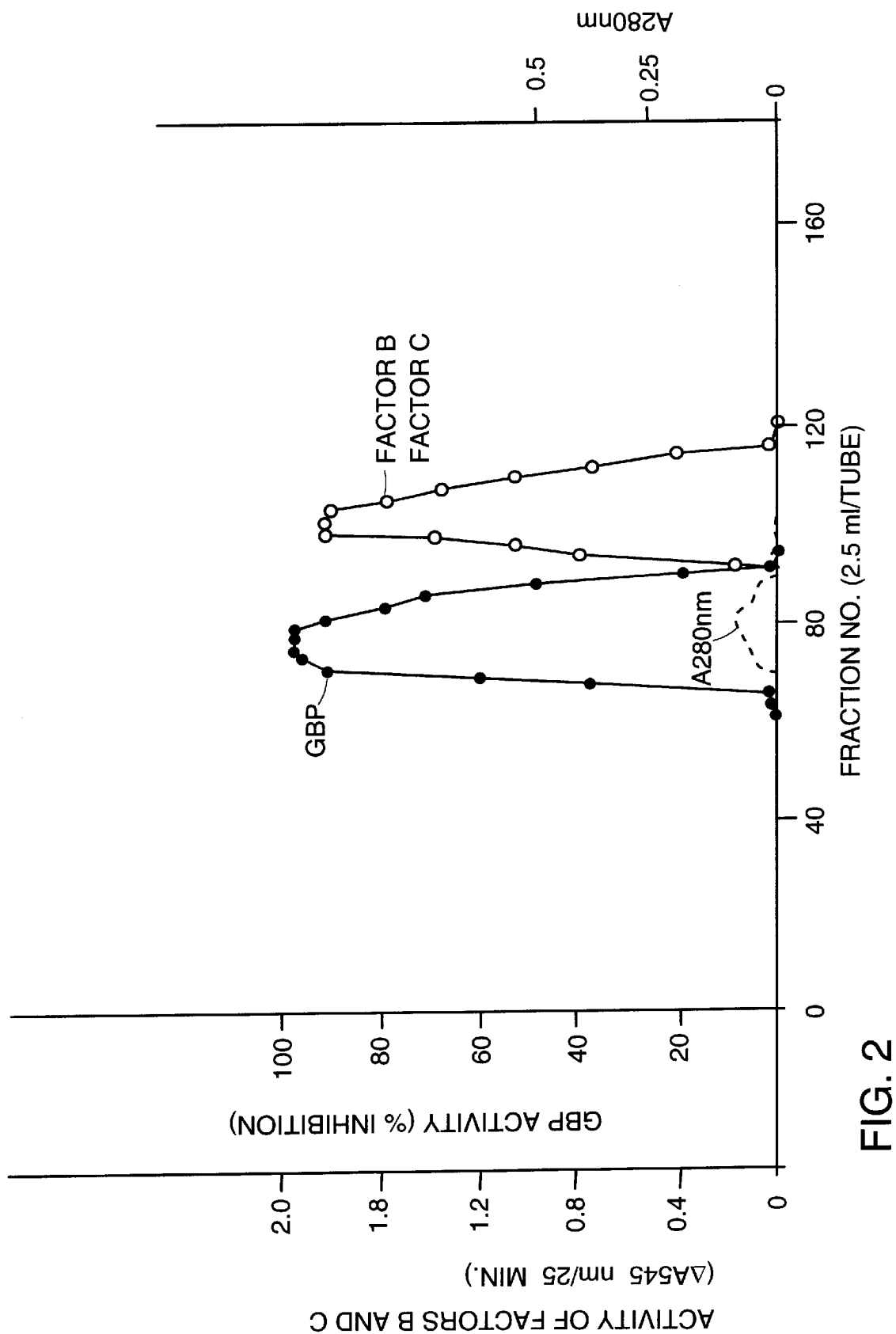
FIG. 2 shows a Sephacryl S-300 HR chromatographic pattern of fraction showing GBP activity of FIG. 1.

The lyophilized fraction was dissolved in 25 ml of water and the whole volume was applied to a Sephacryl S-300 HR column (2.2×95 cm) equilibrated with 0.05M Tris-HCl buffer (pH 8.0) containing 0.5M NaCl and 4 mM CaCl$_2$, and eluted at a flow rate of 18 ml/hr. to give each 2.5 ml fractions. GBP activity was determined as shown above. The required amount for 50% inhibition of factor G activation was defined as 100 units. Hereinafter, the unit of GBP activity is expressed as "units" or "U". The activity of factors B and C was determined by the method of Obayashi et al. (Clin. Chim. Acta, 149, 55–65 (1985)) by determining absorbance at 545 nm. The results are shown in FIG. 2. As shown in FIG. 2, GBP activity was found in fraction Nos. 70–88 (47.5 ml).

Figure 3:
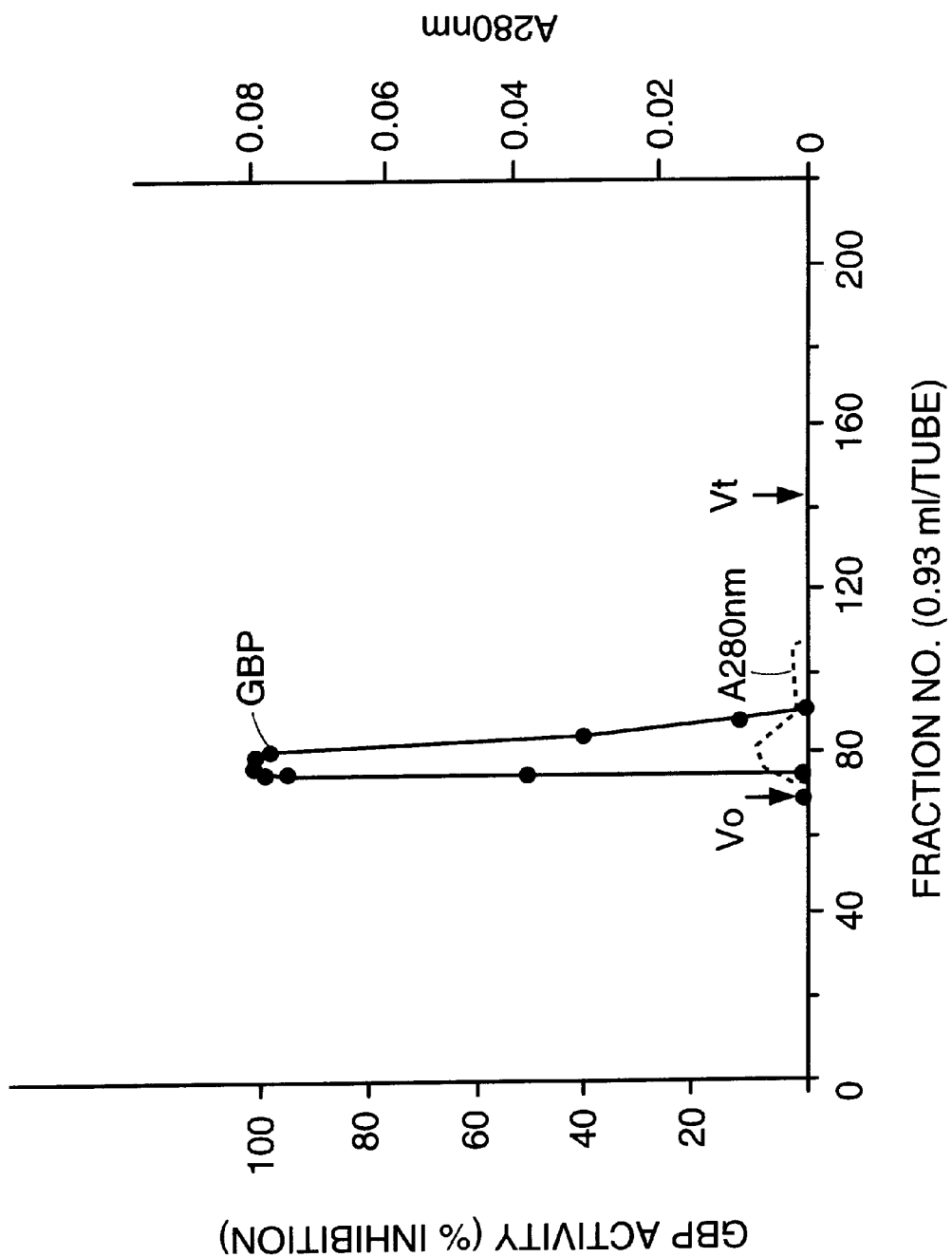
FIG. 3 shows a Sephacryl S-300 HR re-chromatogram pattern of fraction showing GBP activity of FIG. 2.

The fractions were lyophilized, re-dissolved in 8 ml of water and re-applied to a Sephacryl S-300 HR column (1.4–95 cm) equilibrated with the same buffer and eluted at a flow rate of 4.5 ml/hr. to give each 0.93 ml fractions. GBP activity was determined for each fractions and the results are shown in FIG. 3. As shown in FIG. 3, GBP activity was found in fraction Nos. 81–84.

As explained above, GBP can be almost completely separated by treatment with dextran sulfate-Sepharose affinity chromatography (FIG. 1) followed by gel filtration with Sephacryl S-300 HR to separate from factors B and C (FIG. 2), and re-chromatography with a similar carrier to give highly pure GBP. The specific activities in the purification process are shown in Table 1. In crude extract, lysate, a large amount of factor G was existed and assay of GBP activity could not be carried out. The combined chromatographic procedures separated factor G and the presence of GBP and its activity were found for the first time. In addition, said GBP is similarly prepared from lysate of other horseshoe crab (for example, Limulus polyphemus, Tachypleus gigas and Carcinoscorpius rotundicauda).

TABLE 1

| Purification process | Total protein (mg) | Total activity (U) | Specific activity (U/mg) | Yield (%) | Purification rate (-fold) |
|---|---|---|---|---|---|
| Crude extract | 4502.0 | | | | |
| Dextran sulfate-Sepharose CL-6B | 60.8 | $2.13 \times 10^5$ | $3.5 \times 10^3$ | 100 | 1 |
| Sephacryl S-300 (first) | 11.9 | $6.31 \times 10^4$ | $5.3 \times 10^3$ | 29.6 | 1.5 |
| Sephacryl S-300 (second) | 3.5 | $5.95 \times 10^4$ | $1.7 \times 10^4$ | 27.9 | 4.9 |

(2) Physicochemical Properties of GBP (1) Assay of Molecular Weight

Figure 4:
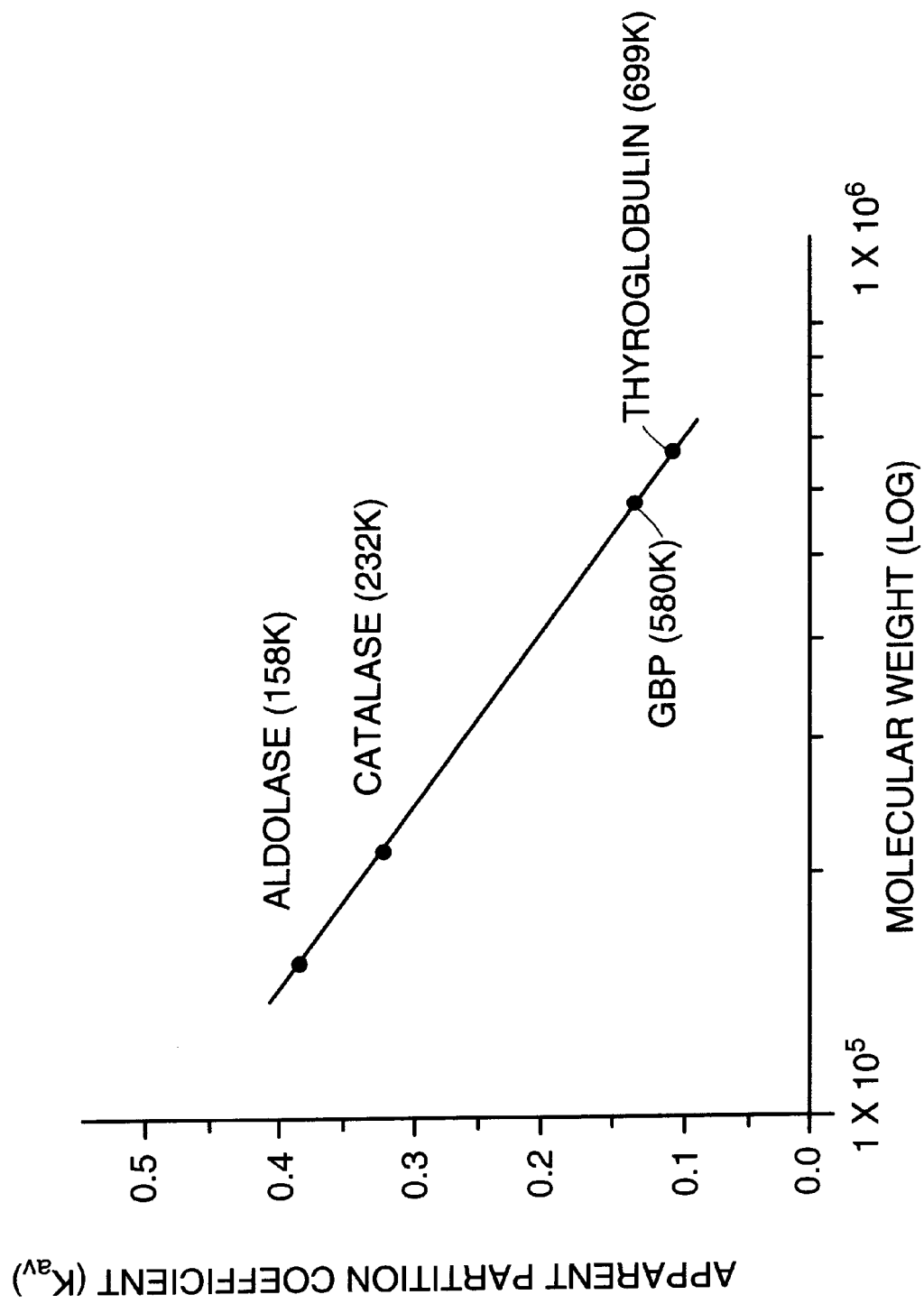
FIG. 4 shows a presumed molecular weight of GBP of the present invention by gel filtration method with Sephacryl S-300 HR.

In the aforementioned Sephacryl 5–300 HR column chromatography (1.4×95 cm) with bed volume (vt) of 146.2 ml, the elution sites (Ve) of GBP active fractions were calculated and apparent partition coefficient (($V_e - V_0/V_t - V_0$), expressed as $K_{av}$) of each protein in High Molecular weight Gel Filtration Kit (produced by Pharmacia) were plotted to logarithms of molecular weight to give a calibration curve to estimate the molecular weight of GBP. The results are shown in FIG. 4, indicating the molecular weight of GBP in GBP active fractions was about 580 k dalton.

Figure 5:
FIG. 5 shows a presumed molecular weight of GBP of the present invention by SDS-PAGE. Lane A and B show a molecular weight marker and molecular weight of GBP under reducing condition, respectively.

In a 0.3 ml volume centrifugal filtration tube with molecular weight cut-off 5,000 (Ultrafree C3LCC, Millipore), 0.3 ml of the purified GBP obtained by the aforementioned procedure (1.9×10$^3$ units/ml, protein concentration of 245.2 μg/ml) was placed and centrifuged at 4,500×g, for 50 min. under cooling at 4° C. to give 0.03 ml of the concentrate. The concentrate was mixed with water to make 0.3 ml volume. The resultant solution was subjected to centrifugal filtration under similar conditions to give a concentrate of 0.03 ml. The resultant sample was analyzed with SDS-PAGE under reducing condition with 2-mercaptoethanol according to the method or Laemmli (Nature, 227, 680–685 (1970)), stained with Coomassie Brilliant Blue R-250 to give molecular weight of about 170 k dalton as shown in FIG. 5.

As markers, 6 proteins (Boehringer Mannheim GmbH) were used.

α$_2$-macroglobulin (170 k), β-galactosidase (116.4 k), fructose-6-phosphokinase (85.2 k), glutamic acid dehydrogenase (55.6 R), aldoluse (39.2 k) and triose phosphoisomerase (26.6 k).

(2) Determination of Isoelectric Point

Figure 6:
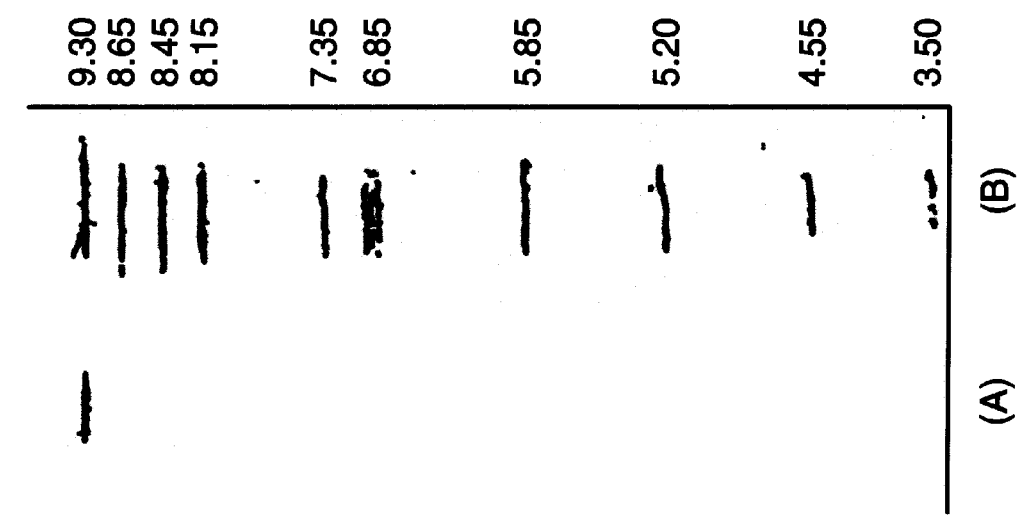
FIG. 6 shows isoelectric point of GBP of the present invention by isoelectric point electrophoresis. Lane A and B show isoelectric point of GBP and that of marker, respectively.

Isoelectric forcing was carried out with PhastSystem™ (Pharmacia) by a conventional method (In Gel Electrophoresis and Isoelectric Focusing of Proteins 236–240 (1984)) using PhastGel IEF gradient 3–9 (Pharmacia). The gel after electrophoresis was stained with Coomassie Brilliant Blue R-250. The results are shown iii FIG. 6. As shown in FIG. 6, GBP showed a single band indicating isoelectrio point (pI) of about 9.2.

As markers, 10 proteins (Pharmacia) were used. Trypsinogen (pI 9.30), lens beans lectin-basic band (pI 8.65), lens beans lectin-medium band (pi 8.45), lens beans lectin-acidic band (pI 8.15), myoglobin-basic band (pI 7.35), myoglobin-acidic band (pI 6.85), bovine carbonic anhydrase B (pI 5.85), β-lactoglobulin (pI 5.20), soybean trypsin inhibitor (pI 4.55) and amyloglucosidase (pI 3.50).

(3) Determination of N-terminal Amino Acid Sequence of GBP

The determination of N-terminal amino acid sequence was carried out according to the method of Mataudaira (J. Biol. Chem. 262, 10035–10038 (1987)). In 7, 5% slab gel, 0.01 ml of GBP ($1.7 \times 10^4$ units/ml ) was applied for one lane and subjected to elertrophoresis at a constant electric current of 30 mA. After electrophoresis, the gel was cut out, washed with water for 5 min., immersed in a transfer buffer (0.01M 3-(cyclohexylamnino)-1-propansulfonic acid (CAPS)/10% methanol) for 15 min. Then, the protein was transfered from gel to a polyvinylidonedifluoride (PVDF) membranes (Bio-Rad Lab.) at 4° C. for 18 hrs. under constant voltage of 20V using transblotting sandwich apparatus. The PVDF membrane was washed with water for 5 min., stained with 0.1% Coomassie Brilliant Blue R-250/50% methanol for 5 min. The stained membrane was washed 3 times with water, dried in a clean room for 1hr. and kept at −35° C. The aimed band was cut with a sterilized knife and analyzed by a connventional method with a gas-phase amino acid sequencer (Shimazu, PPSQ-10).

The following N-terminal amino acid sequence was obtained Lys-Ser-Gly-Phe-Ile-Leu-Thr-Ala-Pro-Lys-Ser-Leu-Thr-Leu-Gly-Arg-Asn-Asn-Arg-Leu-Asn-Leu-His-Leu-Phe-Asp-Ile-Asn-—Thr-Asn-Gly-Phe-xaa-Arg-Ile-Gly-Val-Lys-Asp-Gln-Asn-Asp-Phe-Asn-(SEQ ID NO:1) (wherein, Xaa represents one of naturally occurring amino acids).

(4) UV Spectrum and Properties of GBP.

Figure 7:
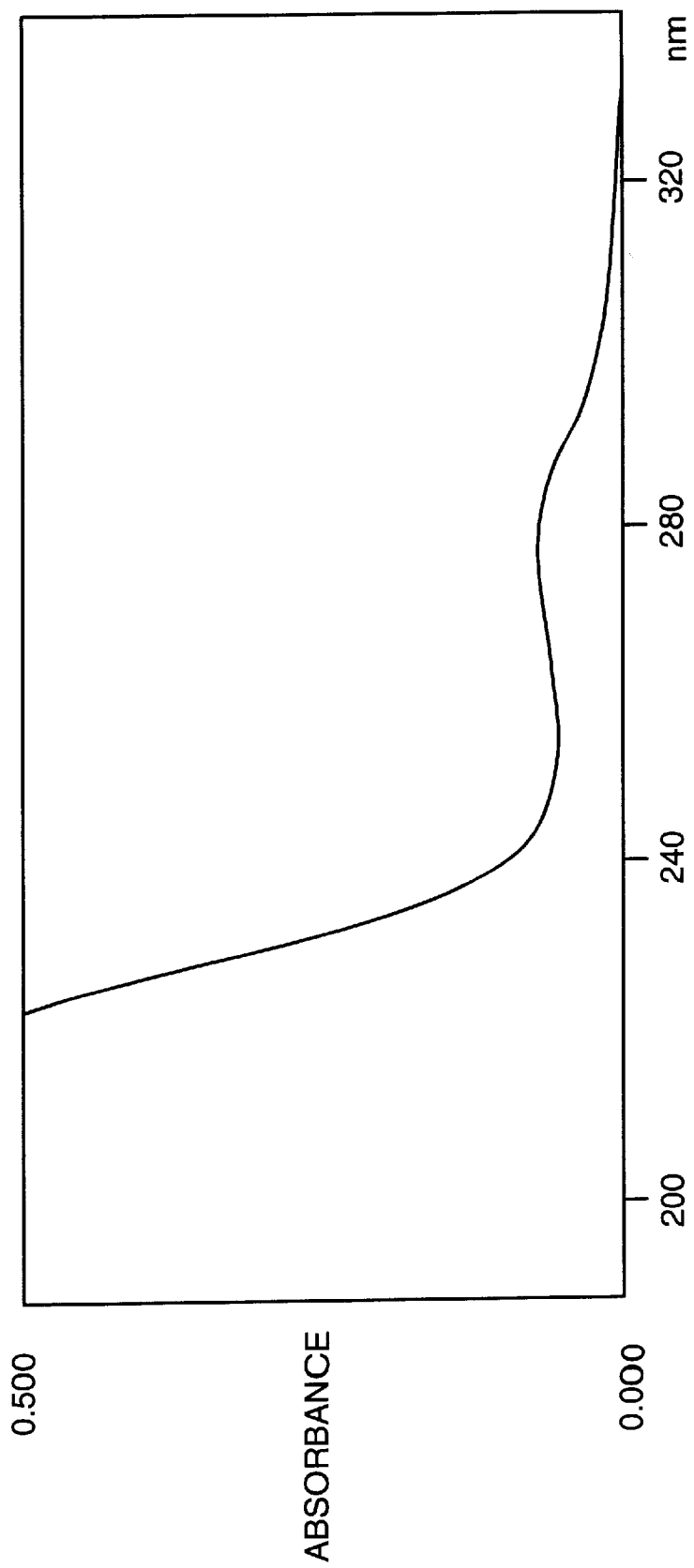
FIG. 7 shows an UV absorption spectrum of GBP of the present invention.

Assay of UV absorption spectrum of the fraction gave a characteristic spectrum having maximum absorption at 280 nm as shown in FIG. 7. The fraction was lyophilized to give easily water soluble white powder.

EXAMPLE 2

Investigation of Action of GBP (1) Inhibitory Activity Against Factor G

Figure 8:
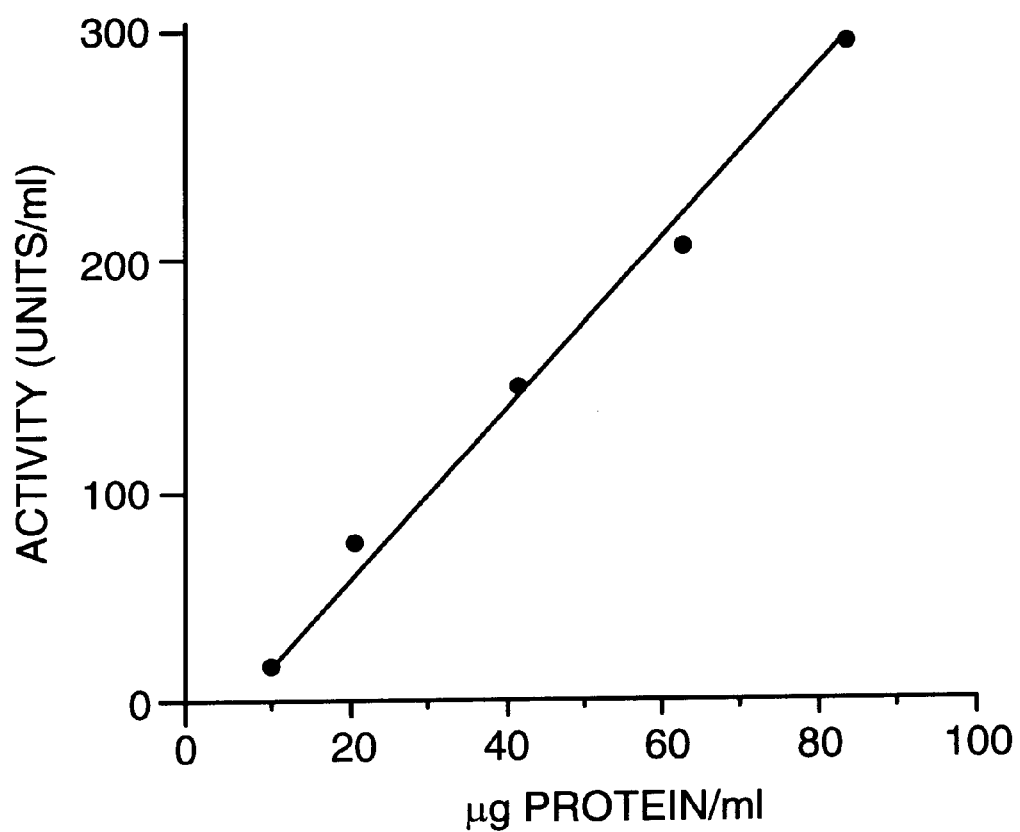
FIG. 8 shows inhibitory ability of factor G activation and doses of GBP of the present invention.

Each 0.05 ml of purified GBP (10, 20, 40, 60, 80 μg/ml) obtained in Example 1 was examined to give inhibitory activity against factor G (GAP activity) by the aforementioned method. The results are shown in FIG. 8. As shown in FIG. 8, GBP activity was clearly dose dependent.

(2) Changes of Activity of GBP by Heat Treatment.

Purified GBP obtained in Example 1 was treated at 100° C. for 3 min and centrifuged at 1,000×g for 15 min. The resultant supernatant was diluted with water to 10-fold. The inhibitory activity against factor G was investigated for a 0.05 ml portion of the diluted solution before and after treatment by the aforementioned method. The results are shown in Table 2.

TABLE 2

| Method | Total activity (U) | Residual activity (%) |
|---|---|---|
| Control (no treatment) | 42.8 | 100 |
| Heat treatment (100° C., 3 min.) | 4.1 | 9.6 |

Table 2 shows that GBP is heat labile (instable against heat) protein.

(3) Binding Specificity of GBP

Straight or branched chain (1→3)-β-D-glucan was added to 0.05 ml of GBP ($1.6 \times 10^4$ units/ml) and GBP activity was determined by the aforementioned method. The residual activity was determined to calculate the inhibitory ratio. The results are shown in Table 3. The sources of straight and branched chain (1→3)-β-D-glucans are shown below. Straight chain (1→3)-β-D-glucan:

Pachyman (prepared by the method described in Agric. Biol. Chem., 32, 1261–1269 (1968))

Curdlan (derived from *Alcaligenes faecalis* var. myxogenes, Wako Pure Chemicals Ltd.)

Carboxymethylated Curdlan (CMPS) (prepared by the method described in Phytochemistry, 1, 175–188 (1962), degree of substitution, 0.63).

Paramylon (derived from *Euglena gracillus*, prepared by the method described in Biochim. Biophys. Acta, 44, 161–163 (1960))

Branched chain (1→3)-β-D-glucan:

(1→6), (1→3)-β-D-glucan: Shizophyllan (Sonifilan; Kaken Pharmaceutical Co., Ltd.), Lentinan (Ajinomoto Co., Ltd.), Laminaran (derived from *Laminaria digitata*, Sigma Corp.), Laminaran (derived from *Eisenia araborea*, Nakarai Tesque).

(1→4), (1→3)-β-D-glucan: Lichenan (derived from *Cetraria islandica*, Sigma Corp.), barley β-D-glucan (Sigma Corp.)

Laminaran, Carboxymethylated Curdlan, Schizophyllan ($2 \times 10^{-6}$ g/ml), Lentinan ($2 \times 10^{-8}$ g/ml), Lichenan and barley β-D-glucan were dissolved in distilled water, Pachyman and Curdlan were dissolved in 0.1M NaOH aqueous solution, Paramylon, Schizophyllan ($1 \times 10^9$ g/ml) and Lentinan ($2 \times 10^{1-10}$ g/ml) were dissolved in 0.3M NaOH aqueous solution, respectively, and suitably diluted with distilled water or 0.01M NaOH aqueous solution for use.

TABLE 3

| Glucan | Type of linkage | Number-average molecular weight (KD) | Glucan concentration (g/ml) | Relative inhibition (%) |
|---|---|---|---|---|
| Pachyman | (1 → 3)-β-D | 80 | $5 \times 10^{-11}$ (0.1M NaOH) | 99.0 |
| Curdlan | (1 → 3)-β-D | >136 | $5 \times 10^{-11}$ (0.1M NaOH) | 98.5 |
| Carboxymethyl Curdlan | (1 → 3)-β-D | >95 | $5 \times 10^{-11}$ (DW) | 99.2 |
| Paramylon | (1 → 3)-β-D | >118 | $2.5 \times 10^{-11}$ (0.3M NaOH) | 99.2 |
| Laminaran derived from *L. digitata* | (1 → 6) (1 → 3)-β-D | 5.85 | $1 \times 10^{-7}$ (DW) | 95.8 |
| derived from *E. arborea* | (1 → 6) (1 → 3)-β-D | 16.8 | $1 \times 10^{-7}$ (DW) | 95.2 |

TABLE 3-continued

| Glucan | Type of linkage | Number-average molecular weight (KD) | Glucan concentration (g/ml) | Relative inhibition (%) |
|---|---|---|---|---|
| Schizo-phyllan | (1 → 6) (1 → 3)-β-D | 76.8 | $1 \times 10^{-9}$ (0.3M NaOH) | 63.6 |
|  | (1 → 6) (1 → 3)-β-D |  | $2 \times 10^{-6}$ (DW) | 60.6 |
| Lentinan | (1 → 6) (1 → 3)-β-D | 94.7 | $2 \times 10^{-10}$ (0.3M NaOH) | 59.4 |
|  | (1 → 6) (1 → 3)-β-D |  | $2 \times 10^{-8}$ (DW) | 57.5 |
| Lichenan | (1 → 4) (1 → 3)-β-D | 22 | $7.5 \times 10^{-7}$ (DW) | 40.7 |
| Barley β-D-glucan | (1 → 4) (1 → 3)-β-D | >23.1 | $1.25 \times 10^{-7}$ (DW) | 36.2 |

DW and NaOH represent solvent for sample. DW and NaOH represent distilled water and sodium hydroxide aqueous solution, respectively.

To 0.025 ml of GBP ($1.6 \times 10^2$ units/ml), 0.025 ml of various polysaccharide solution except for β-glucan was added, warmed at 37° C. for 10 min., 0.025 ml of 100 pg/ml of Pachyman was added, allowed to stand at 37° C. for 10 min Thereafter, 0.04 ml of factor G, 0.02 ml of proclotting enzyme (ProCE) and 0.02 ml of 5 mM Boc-Leu-Gly-Arg-pNA, and 0.01 ml each of 1M $MgSO_4$ and 2M Tris-HCl buffer at pH 8.0 were added, incubated at 37° C. for 20 min. and residual activity was determined to calculate inhibitory ratio. The results are shown in Table 4. The sources of polysaccharides used here are shown below.

(1→4)-β-D-glucan: carboxymethylcellulose sodium salt (Nakarai Tesque)

(1→6)-β-D-glucan: Gyrophoran derived from *Gyrophora esculenta*, prepared according to J. Ferment. Technol., 50, 388–396 (1971).

(1→6)-α-D-glucan: dextran (derived from Leuconostoc sp., molecular weight up to 40,000, Seikagaku Corporation).

(1→4), (1→6)-α-D-glucan: Pullulan (derived from *Pullularia pullulans*, Hayashibara Biochemical).

(1→2), (1→3), (1→6)-α-D-mannan: yeast α-D-mannan (Sigma Corp.)

(1→3)-β-D-xylan: (polyglycoside of xylose, derived from *Caulerpa brachypus*, prepared according to Nature, 187, 82–83 (1960)).

Carboxymethylocllulooe, dextran and pullulan were dissolved in distilled water, gyrophoran was dissolved in 0.1M NaOH aqueous solution, and α-D-mannen and β-D-xylon was dissolved in 0.3M NaOH aqueous solution, respectively. The resultant solutions were suitably diluted with distilled water before use.

TABLE 4

| Glucan | Type of linkage | Glucan concentration (g/ml) | Relative inhibition (%) |
|---|---|---|---|
| Carboxymethyl-cellulose | (1 → 4)-β-D | $1 \times 10^{-7}$ (DW) | 1.5 |
| Gyrophoran | (1 → 6)-β-D | $2 \times 10^{-11}$ (0.1M NaOH) | 1.1 |
| Dextran | (1 → 4)-α-D | $1 \times 10^{-7}$ (DW) | 1.0 |
| Pullulan | (1 → 4), (1 → 6)-α-D | $1 \times 10^{-7}$ (DW) | 1.0 |

TABLE 4-continued

| Glucan | Type of linkage | Glucan concentration (g/ml) | Relative inhibition (%) |
|---|---|---|---|
| Yeast α-D-mannan | (1 → 2), (1 → 3), (1 → 6)-α-D | $1 \times 10^{-8}$ (0.3M NaOH) | 1.2 |
| Xylan | (1 → 3)-β-D | $1 \times 10^{-7}$ (0.3M NaOH) | 1.1 |

DW And NaOH represent solvent for sample. DW and NaOH represent distilled water and sodium hydroxide aqueous solution, respectively.

As shown in Table 3, inhibitory activity of GSP against branched chain (1→3)-β-D-glucan such as (1→6), (1→3)-β-D- and (1→4), (1→3)-β-D-glucan and carboxymethylated (1→3)-β-D-glucan was observed in addition to straight chain (1→3)-β-D-glucan.

Further, the binding activity with (1→3)-β-D-glucan, that is inhibitory activity against factor G of polyseccharides having a structure other than (1→3)-β-D-glucan was determined by addition of GBP beforehand and warming, followed by addition of (1→3)-β-D-glucan to determine the inhibition of (1→3)-β-D-glucan binding. As clearly shown in Table 4, suppression of inhibitory activity was not observed in carboxymethylcellulose ((1→4)-β-D-), gyrophoran ((1→6)-β-D-), dextran ((1→6)-α-D-), pullulan ((1→4), (1→6)-α-D-), yeast α-mannan ((1→2), (1→3), ((1→6)-α-D-) or xylan (polyglycosice of xylose, (1→3)-β-D-).

(4) Detailed Investigation of Factor G Inhibitory Activity of GBP.

Experiment 1: A mixture of 0.04 ml of factor G, 0.02 ml of proclotting enzyme (ProCE), 0.01 ml each of 1M $MgSO_4$ and 2M Tris-HCl buffer (pH 8.0), and 0.05 ml of 50 pg/ml of pachyman (hereinafter may be referred as BG) was warmed at 37° C. for 20 min. and mixed with 0.05 ml of GOP ($1.6 \times 10^4$ units/ml) and 0.02 ml of 5 mM substrate (Boc-Leu-Gly-Arg-pNA: hereinafter may be referred as Sub). The mixture was caused to react at 37° C. for 3 min. and the liberated P-nitroaniline was developed with diazo coupling by a known method (Tamura, H et-al. Thromb. Res. 27, 51–57 (1982)) and absorbance at 545 nm was determined, Experiment 2: To 0.04 ml of factor G, 0.05 ml of GBP was added, warmed at 37° C. for 10 min. and 0.05 ml of 50 pg/ml BG, 0.02 ml of ProCE, 0.01 ml each of 1M $MgSO_4$ and 2M Tris-HCl buffer (pH 8.0), 0.02 ml of 5mM Sub were added and caused to react at 37° C. for 20 min. The reaction mixture was developed by diazo coupling in a similar manner with that of Experiment (1), and absorbance at 545 nm was determined.

Experiment 3: To 0.05 ml of BG, 0.05 ml of GBP was added, warmed at 37° C. for 10 min., then 0.04 ml of factor G, 0.02 ml each of ProCE and 5 mM Sub, 0.01 ml of 1M $MgSO_4$ and 2M Tris-HCl buffer (pH 8.0) were added, caused to react at 37° C. for 20 min. The reaction mixture was developed by diazo coupling in a similar manner with that of Experiment (1). and absorbance at 545 nm was determined.

Experiment 4: To a mixture of 0.04 ml of factor G, 0.02 ml each of ProCE and 5 mM Sub, 0.05 ml of 50 pg/ml BG, 0.01 ml each of 1M $MgSO_4$ and 2M Tris-HCl buffer (pH 8.0), 0.05 ml of GBP was added, caused to react at 37° C. for 20 min. The liberated p-nitroaniline was developed by diazo coupling in a similar manner with that of Experiment 1, and absorbance at 545 nm was determined.

Water was used instead of GBP in each experiment (1)–(4) give control groups and inhibitory ratio of factor G activity (%) was determined. The results are shown in Table 5.

TABLE 5

| Experiment | Procedure | Relative inhibition (%) |
|---|---|---|
| 1 | FG + BG + ProCE (37° C., 20 min.) → + GBP + Sub (37° C., 3 min.) | 0 |
| 2 | FG + GBP (37° C., 10 min.) → + BG + ProCE + Sub (37° C., 20 min.) | 37.5 |
| 3 | BG + GBP (37° C., 10 min) → + FG + ProCE + Sub (37° C., 20 min.) | 100 |
| 4 | FG + BG + GBP + ProCE + Sub (37° C., 20 min.) | 33.4 |

FG: factor G, BG: pachyman ((1 → 3) -β-D-glucan, ProCE: proclotting enzyme, GBP: eluted fraction of dextran sulfate-Sepharose CL-6B with 0.45M NaCl (including the protein of the present invention), Sub: substrate (Boc-Leu-Gly-Arg-pNA).

As shown in Table 5, the protein of the present Invention (GBP) showed a marked elevation of inhibitory activity against factor G activation by mixing in advance with (1→3-β-D-glucan and warming at 37° C. This activity is considered as a direct binding of (1→3)-β-D-glucan and GBP, that is, an inhibition of factor G activation by lectin-like interaction and not by competitive inhibition against (1→3)-β-D-glucan (AG) due to direct binding of an inhibitor of factor G activation (such as low molecular- and water soluble-polyglucoside ("Factor G activation inhibitor"; see WO 90/02951), for example, Laminaran oligosaccharide and curdlan) and factor G. This supports direct binding of the protein of the present invention (GBP) and (1→3)-β-D-glucan.

These results demonstrate that GBP plays important roles in the control and regulation of factor G system triggered by (1→3)-β-D-glucan, in vivo transport of (1→4)-β-D-glucan and growth inhibition of fungi.

EXAMPLE 3

Preparation and Purification of Anti-serum Against GBP

An equal amount of Freund's complete adjuvant (IATRON Laboratories Inc.) was mixed with 500 μl of 400 μg/ml purified GBP aqueous solution and subcutaneously injected to 2 male JW rabbits, body weight 1.8 kg. The similar procedure was repeated 4 times every 2 weeks for sensitization. As a booster, 0.2 ml of 100 μg/ml CBP aqueous solution was intravenously injected. One weed after the final injection, whole blood was drawn from tho rabbits and the blood was allowed to stand at room temperature for 1 hr., then overnight at 4° C. The blood was centrifuged at 2,000 rpm for 5 min. The resultant 60 ml serum was warmed to 56° C. for 5 min. to inactivation and 0.06 g of sodium as azide preservative was added to make 0.1 (w/v) % and to give anti-serum. The antibody titer was determined with Ouchterlony double immunodiffusion method.

Further, said anti-serum was purified by a conventional method of salting out with ammonium sulfate and an affinity chromatography using protein A to give purified immunoglobulin.

Experiment 4

Quantitative Assay of (1→3)-β-D-glucan by Using GBP

Purified GBP aqueous solution (400 μg/ml) was diluted to 1,000-fold with 0.1M NaHCO₃ buffer (pH 9.6) and 50 μl each of the diluted solution was dividedly poured in β-glucan free 96 well microplate (Toxipet plate, Seikagaku corporation), allowed to stand at 4° C. for 12 hrs. to immobilize (adhere) said GBP on the solid phase of plate. Said solution was drawn by suction, wells were washed 3 times with PBS buffer (hereinafter referred as PBS), then, all wells were blocked with PBS containing 5% bovine serum albumin (BSA), warmed at 37° C. for 2hrs. The wells were washed 3 times with PBS containing 0.1% Tween-20 (hereinafter referred as PBS-TW). In the washed wells, 100 μl of (1→3)-β-D-glucan solution (0.1, 1, 10, 100 and 1,000 ng/ml) was added and caused to react at 37° C. for 2 hrs. The wells were washed 3 times with PBS-TW, 100 μl of 0.2 μg/ml of biotin labelled GSP aqueous solution was added and caused to react at 37° C. for 2 hrs. The reaction mixture was mixed with 100 μl of 1 μg/ml peroxidase (HRP) labelled streptavidin and allowed to stand at 37° C. for 2 hrs. Further, 100 μl of substrate solution (10 ml of 50 mM acetate buffer (pH 5.0) containing 10 mg of tetramethylbenzidine and 2 μl of 30% $H_2O_2$) was added and allowed to stand at room temperature for 10 min. The reaction mixture was mixed with 50 μl of 2M sulfuric acid to terminate the reaction, and the absorbance at 450 nm was determined with a microplate reader (Wellreader SK601, Seikagaku Corporation) with a control at 630 nm.

Figure 9:
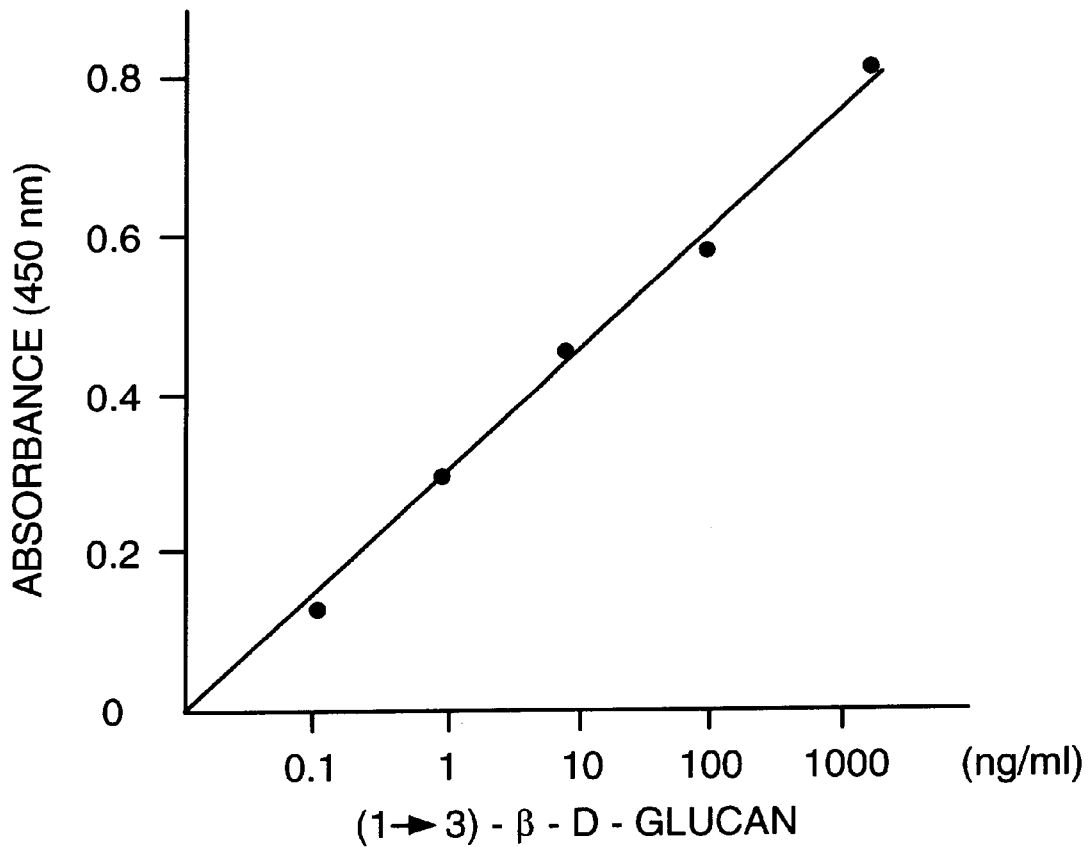
FIG. 9 shows a calibration curve of (1→3)-β-D-glucan concentration and absorbance by the assay method of the present invention.

The dose dependency of (1→3)-β-D-glucan (reactivity with GBP, calibration curve) is shown in FIG. 9.

EXAMPLE 5

Detection of (1→3)-β-D-glucan Using GBP

In 96-well β-glucan free microplate (Toxipet plate 96F, Seikagaku Corporation), 100 μl of an antigen solution containing 1.5 μg of a conjugate of (1→3)-β-D-glucan and bovine serum albumin (BSA) (prepared according to the method described in Agric. Biol. Chem., A, 54, 1953–1959 (1990)) was placed and allowed to stand at 4° C. for 12 hrs. to coat the antigen to the plate. The antigen solution in the wells was drawn by suction. The wells were washed 3 times with PBS, re-filled with PBS containing 5% BGA (hereinafter referred as blocking solution) and incubated at 37° C. for 2 hrs. The blocking solution in the wells was removed and the wells were washed 3 times with PHS containing 0.1% Tween-20 (hereinafter referred as PBS-Tween-20). In the wells, 100 μl of 1 μg/ml GBP aqueous solution wag added, incubated at 37° C. for 2 hrs. The wells were washed with PBS-Tween-20, filled with anti-GRP serum or normal rabbit serum diluted at ratios of 1:5,000, 1;10,000 and 1;50,000 and incubated at 37° C. for 2 hrs. The wells were washed with PBS-Tween-20, filled with peroxidase labelled sheep anti-rabbit IgG serum diluted with PBS at a ratio of 1:1,000, incubated at 37° C. for 2 hrs. The wells were washed with PBS-Tween-20, filled with 100 μl of a substrate solution (10 ml of 50 mmol/L acetate buffer containing tetrdmethylbenzidine 10 mg and 2 μl of 30% $H_2O_2$, pH 5.0) and incubated at room temperature for 10 min. The incubation was terminated by adding 50 μl of 2M $H_2SO_4$ and the absorbance was determined at 450 nm with a microplate reader (wellreader SK601, seikagaku Corporation.) with a control at 660 nm.

Direct binding of GBP and (1→3)-β-D-glucan was experimentally proved as shown above using anti-GBP serum.

The results of the reaction of rabbit anti-GBP serum to the complex of (1→3)-β-D-glucan and GBP are shown in Table 6.

TABLE 6

| Anti-serum | Dilution rate of antibody | Absorbance at 450 nm |
|---|---|---|
| Anti-GBP serum | 1:5,000 | 2.856 |
| | 1:10,000 | 2.632 |
| | 1:50,000 | 0.752 |
| Rabbit serum (control) | 1:5,000 | 0.109 |
| | 1:10,000 | 0.074 |
| | 1:50,000 | 0.016 |

EXAMPLE 6

Removal of (1→3)-β-D-glucan Using GBP

On a glass filter (#2), 100 ml of β-D-glucan free Sepharose 4B (Pharmacia) was placed and washed under aspiration with 2 L of distilled water for injection (hereinafter referred as DW). The solution was placed in a 1 L volume beaker and mixed with 200 ml of DW. The resultant mixture was adjusted to pH 11–12 using 10N NaOH with stirring by a magnetic stirrer and 25 g of cyanogen bromide (CNBr) in 500 ml of DW was gradually added till pH of the reaction mixture shows no change. The resultant CNBr activated Sepharose 4B was filtered with a glass filter, washed with 2 L of cold water and 1 L of 0.1M NaHCO$_3$. In 10 ml of the activated Sepharose 4B, 2 mg of lyophilized and pulverized GBP was added to make its concentration 0.2 mg/ml and treated at 4° C. for 24 hrs. while stirring with rotator. After the reaction, the residual impurity, imidocarbonate, was inactivated in 0.2M Tri-HCl buffer, pH 8.0, for 5 hrs. To 0.5 g of GBP immobilized Sepharose 4B, (1→3)-β-D-glucan solution (0.1, 1.0, 10 or 100 μg/ml) was added and stirred with multi shaker for 8 hrs. The reaction mixture was centrifuged at 3,000 rpm for 10 min. To 50 μl of the resultant supernatant, 50 μl of (1→3)-β-D-glucan specific synthetic substrate (Gluspecy, Seikagaku Corporation.) was added to determine residual (1→3)-β-D-glucan in the supernatant, Similar experiment was carried out without using the carrier to give control value of 100% and the removal ratio of (1→3)-β-D-glucan was calculated. The results of removal of (1→3)-β-D-glucan using GBP immobilized carrier are shown in Table 7.

TABLE 7

| (1→3)-β-D-glucan Before treatment | (μg/ml) After treatment | Removal ratio (%) |
|---|---|---|
| 0.1 | 0 | 100 |
| 1 | 0 | 100 |
| 10 | 0.01 | 99.9 |
| 100 | 0.08 | 99.9 |

Industrial Applicability

As explained above, (1→3)-β-D-glucan binding protein and an antibody which recognizes the protein specifically detects endotoxin and (1→3)-β-D-glucan in samples or efficiently removes (1→3)-β-D-glucan in samples. The (1→3)-β-D-glucan binding protein, the antibody of the present invention can be used as detection agent and removing agent of these substance. Thus, these can be used to detect and detoxicate these substances in samples.

Further, the (1→3)-β-D-glucan binding protein of the present invention may bind (1→3)-β-D-glucan in main component polysaccharide of fungal cell wall and is expected to be developed as medicines, particularly as an antifungal agent.

---

---

What is claimed is:

1. A purified *Tachypleus tridentatus* protein which exhibits a single band in polyacrylamide gel electrophoresis (PAGE), and comprises the following physicochemical properties:

specifically binds to (1→3)-β-D-glucan;
  (1) a molecular weight of about 580 k dalton as determined by a gel filtration method under non-reducing conditions, and a molecular weight of about 170 k dalton as determined by sodium dodecylsulfate-polyacrylamide gel electrophoresis (SDS-PAGE) under reducing conditions;
  (2) an isoelectric point of about 9.2;
  (3) a UV absorption spectrum maximum at 280 nm;
  (4) easily soluble in water; and
  (5) a white color,
wherein said protein inhibits factor G activation.

2. The purified protein according to claim 1 having the following N-terminal amino acid sequence:
  Lys-Ser-Gly-Phe-Ile-Leu-Thr-Ala-Pro-Lys-Ser-Leu-Thr-Leu-Gly-Arg-Asn-Asn-Arg-Leu-Asn-Leu-His-Leu-Phe-Asp-Ile-Asn-—Thr-Asn-Gly-Phe-Xaa-Arg-Ile-Gly-Val-Lys-Asp-Gln-Asn-Asp-Phe-Asn-(SEQ ID NO:1)

wherein, Xaa represents a naturally occurring amino acid.

3. The purified protein according to claim 1 or 2 wherein said protein is derived from amoebocytes.

4. An agent for assaying (1→3)-β-D-glucan, said agent comprising the purified protein according to claim 1 or 2.

5. The assay agent according to claim 4 wherein said protein is labeled with a labeling substance.

6. A kit for assaying (1→3)-β-D-glucan, said kit comprising the protein according to claims 1 or 2, and an antibody which selectively recognizes said protein.

7. The assay kit according to claim 6 wherein the antibody is labeled with a labeling substance.

8. A kit for assaying (1→3)-β-D-glucan, said kit comprising the protein according to claim 1 or 2, and an assay agent comprising said protein labeled with a labeling substance.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 44 amino acids
        (B) TYPE: amino acid
        (C) STRANDEDNESS:
        (D) TOPOLOGY: linear (ii) MOLECULE TYPE: protein (vi) ORIGINAL SOURCE:
        (C) INDIVIDUAL ISOLATE: Horseshoe crab
        (G) CELL TYPE: Amoebocytes (xi) SEQUENCE DESCRIPTION: SEQ ID NO:1:

```
Lys Ser Gly Phe Ile Leu Thr Ala Pro Lys Ser Leu Thr Leu Gly Arg
1               5                   10                  15

Asn Asn Arg Leu Asn Leu His Leu Phe Asp Ile Asn Thr Asn Gly Phe
            20                  25                  30

Xaa Arg Ile Gly Val Lys Asp Gln Asn Asp Phe Asn
            35                  40
```